United States Patent [19]
McQuigg et al.

[11] Patent Number: 6,137,004
[45] Date of Patent: *Oct. 24, 2000

[54] PROCESSES FOR RECOVERING CITRIC ACID

[75] Inventors: Donald W. McQuigg, Mooresville, Ind.; Charles Marston, Midland, Mich.; Gina Fitzpatrick, Indianapolis, Ind.; Ernest Crowe, Beech Grove, Ind.; Susan Vorhies, Indianapolis, Ind.

[73] Assignee: Reilly Industries, Inc., Indianapolis, Ind.

[ * ] Notice: This patent is subject to a terminal disclaimer.

[21] Appl. No.: 08/485,348

[22] Filed: Jun. 7, 1995

Related U.S. Application Data

[63] Continuation of application No. 08/026,627, Mar. 4, 1993, abandoned, which is a continuation-in-part of application No. 07/669,490, Mar. 14, 1991, abandoned.

[51] Int. Cl.$^7$ .................................................. C07C 51/42
[52] U.S. Cl. ............................................................ 562/580
[58] Field of Search ............................................... 562/580

[56] References Cited

U.S. PATENT DOCUMENTS 4,851,573  7/1989  Kulpranthiapanja et al. .......... 562/580

*Primary Examiner*—Keith D. MacMillan
*Attorney, Agent, or Firm*—Woodard, Emhardt, Naughton, Moriarity & McNett

[57] ABSTRACT

Described are preferred processes for recovering citric acid from a medium in which it is contained. The citric acid is recovered both effectively and in a form which is readily purifiable. In one preferred process, the citric acid-containing medium is contacted with a solid-phase free base resin having tertiary amine groups to adsorb the citric acid. The citric acid is then desorbed by displacement with a stronger acid, and a citric acid-containing fraction is collected substantially free from contamination by the stronger acid. In another preferred process, a citric acid-containing medium is contacted with a solid-phase divinylbenzene-crosslinked polymer having pyridine or aliphatic tertiary amine functions to adsorb citric acid, the contacting being at a temperature below about 40° C. Adsorbed citric acid is then desorbed with hot $H_2O$ at a temperature of at least about 75° C. Unnecessary impurities such as those arising from the use of organic solvent or throughput inorganic acid desorbents are thereby avoided while at the same time achieving a commercially attractive recovery of the citric acid. Additional preferred modes and process features are also described.

40 Claims, No Drawings

PROCESSES FOR RECOVERING CITRIC ACID

REFERENCE TO RELATED APPLICATION

This application is a continuation of application Ser. No. 08/026,627, filed Mar. 4, 1993, abandoned which is a CIP of Ser. No. 07/669,490, filed Mar. 14, 1991 abandoned.

BACKGROUND

This invention relates generally to processes for recovering citric acid, and more particularly to such processes involving adsorption and desorption of citric acid to and from a solid-phase polymer.

By way of further background, citric acid is a biologically occurring material which finds primary use in the food industry. It has gained worldwide acceptance as a food ingredient, and, has a pleasant acid taste and high water solubility which have motivated its most extensive food application in beverages, jams, jellies, and sweets. Additional uses of citric acid are also prevalent. For instance, it is used in the pharmaceutical and cosmetics industries, in the plastics industry as a raw material for the manufacture of citric acid ester plasticizers, as well as more recently finding substantial use in the preparation of detergents and other cleaning agents.

Since the early work of C. Wehmer beginning in the 1890's, there has been substantial interest and investment in fermentation processes for producing citric acid. As such, nearly all of the 700 million pounds or more of citric acid produced worldwide yearly are from fermentation processes, for instance by the fermentation of a carbon source such as molasses with the microorganism, *Aspergillus niger*. Typically, broths from such fermentations will contain about 10 weight % or more citric acid, as well as about 1000 ppm or more salts, about 1 weight % carbohydrates, and 2 weight % proteins, amino acids and other materials.

As will be appreciated, the recovery of the citric acid product from such mediums has itself been the subject of substantial attention in the academia and industry. In general, three techniques have been used to date, those being precipitation, solvent extraction and solid-phase polymer adsorption and subsequent desorption. As to the first technique, precipitation, it can be fairly stated that it has been the more preferred technique used on a commercial scale, even though significant endeavors as to the other two techniques have been made. In precipitation, calcium hydroxide (lime) is usually added to the fermented medium to form the slightly soluble tricalcium citrate tetrahydrate. Properly performed, this precipitation leaves most impurities in the solution. Impurities may further be removed by washing the filtered precipitate. To further purify the product, the moist precipitate is reacted with sulfuric acid to yield calcium sulfate (gypsum) and a solution of free acid. The free acid solution is then treated with activated carbon and ion exchange resins before evaporation to the crystalline citric acid product. As is recognized, the efficacy of this precipitation method is highly dependent on properly and carefully performing the various steps involved. It is thus a sensitive process requiring high refinement, especially on a commercial scale.

A second technique which has been used to recover citric acid is solvent extraction. In this technique, citric acid is extracted from the fermentation broth with solvent hydrocarbons, for example, octane, benzene, kerosene, ethers, esters, ketones or amines. Citric acid is then reextracted from the solvent phase into water with either the addition of heat or the formation of a citric acid salt. However, this solvent extraction technique is also expensive and complex. Further, solvent extraction generates a very substantial amount of waste for disposal, which from both cost and environmental standpoints is unattractive.

A third technique which has been suggested but to applicants' knowledge not applied on a commercial scale involves the use of solid adsorbents to remove citric acid from the medium. The adsorbed citric acid is then recovered from the polymer utilizing a desorbing agent. For example, U.S. Pat. No. 4,323,702 to Kawabata et al. describes a process for recovering carboxylic acids with a material of which the main component is a polymeric compound having a pyridine skeletal structure and a cross-linked structure. As the patent directs, the captured carboxylic acids are then desorbed using an aliphatic alcohol, an aliphatic ketone or a carboxylic ester as the desorbing agent.

U.S. Pat. No. 4,720,579 to Kulprathipanja describes a process in which citric acid is separated from a fermentation broth using an adsorbent of a neutral, noniogenic, macroreticular, water-insoluble cross-linked styrene-poly (vinyl)benzene. In this patent, a number of pulse tests were run using the described adsorbents. In these tests, a helical column was filled with the adsorbent, and a liquid described as the desorbent passed through the column. At a convenient time, a pulse of feed containing known concentrations of citric acid and other components was injected into the column. The manner in which the injected materials came off the column was then studied. For example, several tests were run in which water was passed through the column, although the patent cautioned that using water, increased desorption temperatures so as to cause premature deactivation of the adsorbent were required. Thus, the patent described a solution to this problem which included adding acetone in about 1 to 15% to the water as desorbent.

In U.S. Pat. No. 4,851,573 to Kulprathipanja et al., another process is described in which an adsorbent of a cross-linked acrylic or styrene resin matrix having attached tertiary amine functional groups or pyridine functional groups is used as an adsorbent. Exemplified in the patent are again pulse tests similar to those described in the above-identified Kulprathipanja '579 patent, this time at temperatures of 60° to 75° C. The adsorbents exemplified included an acrylic resin having attached modified tertiary amines groups functionalized with sulfate ions, and polystyrene resins having attached pyridine groups functionalized with sulfate ions. The patent exemplified addition of sulfuric acid to citric acid solutions prior to the adsorption step, which helps drive functionalization to completion. The Kulprathipanja '573 patent further identifies sulfuric acid and other inorganic acids and water as desorbents, but directs a strong preference for the dilute sulfuric acid because others will be "found to be less effective" and specifically in some cases states that water "is not strong enough to recover the absorbed citric acid quickly enough to make the process commercially attractive."

In still another patent, U.S. Pat. No. 4,851,574, Kulprathipanja describes separating citric acid from a fermentation broth using an adsorbent of a cross-linked acrylic or styrene resin matrix having attached aliphatic quaternary amine functional groups. Again, pulse tests are exemplified, in which sulfuric acid is demonstrated as a desorbent. These pulse tests were conducted at temperatures ranging from 50° to 60° C.

In light of the above and other literature, there remains a need for a highly commerically attractive process for recovering citric acid from a fermentation broth or other medium, by which the citric acid is recovered in a form that is readily purifiable and free from unnecessary organic or inorganic impurities which need be removed. The above-described work by Kawabata utilized organic solvents as desorbing agents which need be removed, thus adding expense and complication to the purification process. Moreover, where alcohol is used as desorbent, upon concentration of the desorbed medium or evaporation of solvent, significant esterification occurs thus leading to additional undesirable impurities in the product. The above-described work by Kulprathipanja et al. harbors instability due to the resins used, and clearly directs that preferred desorbents include either inorganic acids or organic solvent materials which are processed through the column along with the citric acid product and thereby substantially contaminate the same and necessitate significant additional purification measures. Advantageous processes are therefore needed utilizing resins which minimize possible impurities in the product, as well as avoid the need to purify substantial amounts of inorganic acid desorbents such as sulfuric acid or organic desorbents such as aliphatic alcohols, ketones and carboxylic esters from the product. The applicants' invention addresses these needs and provides for the first time commercially attractive processes employing highly stable adsorbents as well as desorbent steps which minimize the opportunity for unnecessary impurities in the desorbed product and greatly simplify workup procedures.

SUMMARY OF THE INVENTION

Accordingly, the present invention provides in one preferred embodiment a process for treating a medium to recover citric acid therein contained. This process includes contacting the medium with a solid-phase free base polymer having tertiary amine functions to adsorb the citric acid. The citric acid is then desorbed by displacement with a stronger acid, e.g. $H_2SO_4$ or HCl, and a citric acid-containing fraction is recovered substantially free from contamination by the stronger acid.

Another preferred embodiment of the invention provides a process for treating a medium to recover citric acid therein contained, with good desorption capacity and regenerability of a polymer adsorbent. The process includes the steps of passing the citric acid-containing medium through a contact zone filled with a particulate solid-phase divinylbenzene-crosslinked polymer having attached pyridine functions or attached aliphatic tertiary amine functions. During the passing step, the citric-acid containing medium is at a temperature below about 40° C. so as to adsorb citric acid on the polymer, and the passing is continued until the polymer in the contacting zone is substantially fully loaded with citric acid. The process also includes the step of desorbing the adsorbed citric acid with hot $H_2O$ at a temperature above about 75° C. so as to provide a desorbed aqueous medium containing at least about 5% by weight citric acid, and wherein the particulate divinylbenzene-crosslinked polymer having attached pyridine functions or attached aliphatic tertiary amine functions is stable against physical degradation under the conditions of the desorbing step.

The applicants have now surprisingly discovered that these inventive processes provide preparations of high commercial and technical attraction. The adsorbent pyridine and other free base resins exhibit good capacity as well as regenerability after performance of the process. In addition, the adsorption/desorption processes provide desorbate product mediums rich in citric acid without the presence of substantial organic solvents or inorganic acids in the desorbate which complicate further processing. Further, these processes have proven unexpectedly effective in reducing ash and readily carbonizable impurity content in the desorbed product.

These and additional features, objects and advantages of the invention will be apparent from reading the following description and appended claims.

DESCRIPTION OF THE PREFERRED EMBODIMENTS

For the purposes of promoting an understanding of the principles of the invention, reference will now be made to certain preferred embodiments and specific language will be used to describe the same. It will nevertheless be understood that no limitation of the scope of the invention is thereby intended, such alterations, and further modifications or applications of the principles of the invention as described herein being contemplated as would normally occur to one skilled in the art to which the invention relates.

As indicated above, preferred embodiments of the invention relate to processes for recovering citric acid from mediums in which it is contained. By the inventive processes, the citric acid is effectively recovered in highly enriched mediums free from significant impurities and readily processible to obtain a purified citric acid product.

As to the medium itself, it will typically be a fermentation broth containing water, citric acid, salts, amino acids and other various components in minor amounts. Usually, the medium will contain citric acid at a level of about 10 wt % or more, and the salt concentration will typically be about 1000 ppm or more. Ordinarily, amino acids and other various materials account for about 2% by weight or less of the medium. As stated previously, the broth may be from a fermentation of a carbon source (e.g. carbohydrates such as corn sugar or molasses) with a suitable microorganism such as *Aspergillus niger*. Other citric acid-containing mediums will also be suitable, and removal of citric acid therefrom is also contemplated as being within the spirit and scope of the present invention.

As to the method of contacting the medium and adsorbent, this can be done in any suitable manner as those practiced in the area will appreciate. For instance, either fixed, moving or fluidized bed systems can be used to provide batch, semi-continuous or continuous processes. A fixed bed is preferably alternately contacted with the medium and the water desorbent, each of which can be passed for example upflow or downflow through a resin bed. In a preferred mode, two or more fixed beds are provided in a system appropriately constructed and valved to reversibly contact one bed with the medium and another with desorbent and/or materials for rinsing or regenerating the resin. In this manner, continuous recovery processes can be conducted. Other contacting systems, for example countercurrent moving bed or simulated moving bed systems, can also be used within the skill of the ordinary artisan. One preferred contacting system is the ISEP™ Continuous Contactor available from Advanced Separations Technology, Inc., Lakeland, Fla.

The adsorption step is preferably conducted at a temperature below about 40° C. At these lower temperatures, the medium containing citric acid is contacted with the free base polymer having tertiary amine functions which is highly effective for adsorbing the acid. The adsorption step is more desirably conducted at temperatures of about 25° C. or below, for instance at near ambient temperatures or below, to maximize adsorption of citric acid by the resin. For lower temperatures, cooling can be provided as necessary to achieve the desired temperature. Of course, the temperature of the contacting in any event will be sufficiently high to prevent freezing of the medium. In more preferred processes, the medium is passed either upflow or downflow through a resin bed at a rate of about 2 to about 12 bed volumes per hour, and more preferably about 4 to 6 bed volumes/hour. The most desirable throughput will vary with the particular resin and other conditions used, as well as process economics involved, as will be determinable by those practiced in the field.

The medium containing citric acid is preferably passed through the resin bed for a time sufficient to achieve substantial or complete saturation of (or full loading of) the resin bed. That is, until the bed has substantially or essentially ceased adsorbing citric acid from the medium. For instance, this resin saturation can be monitored by measuring the pH of the influent and effluent to and from a column containing the resin, with the resin being considered to be saturated when the influent and effluent exhibit the same or substantially the same pH. In this mode of operation, there will of course be some citric acid which passes through and is not adsorbed to the resin, and the medium in which it is contained can be recycled into the column feed if desired.

The preferred free base polymer used in this embodiment of the invention exhibits superior capacities for adsorbing the citric acid. The polymer is solid-phase, that is, it remains a solid in each step of the recovery process including for instance the adsorption, rinse and desorption steps. In this regard, polymers having either N-aliphatic or N-heterocyclic tertiary amine functions can generally be used. For example, AMBERLYST® A-21 resin from Rohm and Haas, Philadelphia, Pa. can be used in the invention. This A-21 resin is crosslinked by divinylbenzene (greater than 2%) and contains aliphatic tertiary amine functions (particularly, an attached dimethylamino group). For additional information about this and other similar resins, reference can be made to the literature including that available from the manufacturer. See, e.g., AMBERLYST A-21® technical bulletin fluid process chemicals,"Rohm and Haas, April 1977. More preferred have been polyvinylpyridine polymers such as poly 2- and poly 4-vinylpyridine free base gel or macroreticular resins exhibiting a bead form. These resins are preferably at least about 2% cross-linked, and more preferably at least about 8% cross-linked with a suitable cross-linking agent, desirably divinylbenzene. More preferred resins to date have been 2 to 25% crosslinked bead-form poly 2- and poly 4-vinylpyridine polymers. For example, preferred polymers in work to date have been poly 2- and poly 4-vinylpyridine resins available from Reilly Industries, Inc., Ind., Indiana, in the REILLEX™ polymer series. These REILLEX™ polymers are 2% or 25% crosslinked, and exhibit good thermal stability and adsorptive and desorptive capacities and other preferred features as described herein. For example, preferred resins of this type have exhibited desorptive capacities of at least about 200 mg citric acid per gram of polymer. Additional preferred resins are available from this same source under the REILLEX™ HP polymer series. These REILLEX™ HP polymers exhibit advantageous capacity as demonstrated in Example 1 below. Further, REILLEX™ HP polymers have proven to be highly regenerable for example by processes similar to Example 6 below. For more information about these REILLEX™ polymers, reference can be made to the literature, including that available from Reilly Industries, Inc. in the form of REILLEX™ reports 1, 2 and 3, which are hereby incorporated by reference in all aspects relevant and material to the invention.

The preferred resin beads can be of any suitable mesh size, for instance preferably about 20 to 60 mesh. Further, the resins can include a minor amount of functionalization of their pyridine groups, which minor amount can include for example functionalization to pyridine N-oxide or guaternary salt species. This functionalization in the applicants' work has been incorporated to modify the relative basicity of the non-functionalized pyridine groups and thereby modify their adsorptive and desorptive properties.

As to the desorption step, as stated, it is performed in one embodiment using an acid stronger than citric acid, desirably $H_2SO_4$ or HCl. The stronger acid solution can be used at any suitable temperature including ambient or elevated temperatures up to about 100° C., e.g. about 75 to about 100° C. The stronger acid displaces the citric acid on the polymer adsorbent and the eluting citric acid is collected in a fraction free from any substantial contamination by the stronger acid (e.g. this fraction preferably contains about 5% by weight or less of the stronger acid, more preferably 1% or less). This can be achieved, for instance, by monitoring the pH of the influent and effluent from the polymer bed, and discontinuing the desorption when the effluent pH indicates significant presence of the stronger acid. As an example, when 5% $H_2SO_4$ is used as desorbent, the desorption can be stopped when the effluent pH drops below about 1.

In another preferred embodiment of the invention, wherein the free base polymer is crosslinked with divinylbenzene and contains pyridine functions or aliphatic tertiary amine functions, the desorption is conducted at a temperature above about 75° C., with $H_2O$. In this regard, the 75° C. temperature can be attained in any manner suitable. For example, the $H_2O$ desorbent can simply be preheated to the necessary temperature prior to contacting with the resin. Additionally, as demonstrated in Examples 1–3 below, the water can be contacted with the resin in a suitable column or vessel having a jacket, and a hot fluid can be circulated through the jacket until the column internal temperature reaches the desired temperature. More preferred temperatures have been at least about 85° C., and temperatures even higher can be used, for instance temperatures of about 85–150° C. and above can be used with steam and/or under pressure. For instance, Example 8 sets forth the results of a steam desorption of citric acid. As reported in the Example, after only 3 bed volumes of water (in the form of steam) had been passed through a citric-acid loaded resin, 33% of the citric acid had been removed.

Another aspect of this embodiment is the high stability and reversibility of the resins employed under the citric acid adsorption/desorption processing conditions. The applicants have discovered that the divinylbenzene-crosslinked polymers are stable against physical degradation even upon repeated citric acid adsorption/hot water desorption cycles. At the same time, the preferred divinylbenzene-crosslinked polymers provide consistently good reversibility and enriched citric acid desorbate mediums. It is vital to process economics that the citric acid recovery process provide for long-term efficacy of the adsorbate resin and highly enriched desorbate mediums. Otherwise, resin costs and energy costs associated with concentrating the desorbate medium undermine commercial process potential. Additionally, breakdown of the polymer adsorbent results in fines passed into the desorbed medium, and degrades the flow and handling properties of the polymer.

In the applicants' preferred processes it is also desirable to rinse the polymer after it is saturated with citric acid and prior to the desorption step. In this regard, the rinse is preferably conducted with water, and at a temperature sufficiently low that no substantial loss of the citric acid from the resin is incurred during the rinse step. Preferred temperatures have been about 15° C. or below, more preferably about 5° C. or below. It is also desirable that the rinse water be adjusted to exhibit a pH of about 4.5 or less to help prevent undue loss of citric acid during the rinse step. In another feature of the invention, this pH adjustment is accomplished by adding $CO_2$ to the rinse water, for instance by adding dry ice to the water at low temperatures at which sufficient $CO_2$ is dissolved to achieve the desired pH. The rinse step is advantageously conducted with about 1 or more bed volumes of water, which are passed either upflow or downflow through the bed at a rate of about 15–20 bed volumes per hour. In any event, preferred rinse steps are conducted so as to remove at least substantially all of the salts or other non-adsorbed impurities which may be caught up in the resin bed.

In preferred processes the desorbent (hot water or stronger acid solution) is used in a volume so as to obtain a final desorbed medium containing at least about 2% by weight citric acid, and more preferably at least about 5% by weight citric acid. For example, in preferred hot water desorptions at about 850 to 100° C. and using preferred resins, approximately 1.5 bed volumes of desorbent water and durations of about 5 to about 20 minutes have provided final desorbed mediums containing about 5% by weight or more citric acid. Similarly, using 10% sulfuric acid desorbent, about 3 bed volumes passed at a flow rate of about 4 to 6 bed volumes/hour have provided desorbed mediums containing about 5% or more citric acid. Of course, other factors will contribute to this finally-obtained concentration, for instance the particular resin used, its extent of saturation with citric acid, etc. Having the benefit of the disclosure herein, those skilled in the art will be readily able to manipulate these and other similar parameters to obtain the preferred citric acid levels in the final desorbed medium.

The preferred processes of the invention have also provided desorbed citric acid mediums of unexpectedly reduced levels of ash and readily carbonizable impurities (RCS). For example, preferred process have reduced ash and RCS content by at least about 65% each, more preferably at least about 80%, and in highly desirable processes about 90% or more. These qualities are highly significant from both technical and commercial standpoints, and further demonstrate the surprising nature and advantage of the applicants' discoveries.

While the invention has been described in detail in the foregoing paragraphs, the same is to be considered as illustrative and not restrictive in character, it being understood that only the preferred embodiments have been described and that all changes and modifications that come within the spirit of the invention are desired to be protected. The following specific Examples are given in further explanation and description of these embodiments, but are intended to be exemplary and not limiting thereof.

EXAMPLE 1

Desorption Capacity for REILLEX™425 and HP Resins

The citric acid desorption capacity was determined for various polyvinylpyridine polymers by first saturating the polymers with citric acid, desorbing the adsorbed citric acid with hot water, and measuring the amount of citric acid removed. Accordingly, 10 wt % citric acid solutions were prepared and their concentrations accurately determined by titrating with 0.1N NaOH to a phenolphthalein endpoint.

The resin to be tested was sieved to give a 20 to 60 mesh fraction. 30 to 50 cc portions of the resin were accurately weighed out and slurried with water in a jacketed 1" diameter ion-exchange column with volume markings. After the resin swelled and settled, the water level was lowered to the top of the resin bed and the resin's volume determined. Another sample of the resin from the same mesh fraction was weighed, dried to a constant weight at 70° C. vacuum under reduced pressure, and its loss-on-drying (L.O.D.) determined. The L.O.D. was used to calculate the dry weight of resin packed in the column.

The prepared citric acid solution was passed downflow through the resin bed at a moderate rate (5 to 10 bed volumes an hour) until the resin was saturated as determined by the effluent concentration equaling that of the influent. The liquid level was drained to the top of the resin bed, and the resin was rinsed downflow with one bed volume of cold ($\leq 5°$ C.) $CO_2$ saturated water with a pH less than 4.5. This rinse water had been prepared by adding dry ice to water. Compressed air was blown through the bed to dry the resin. The entire column effluent and rinses were combined, purged with nitrogen to remove $CO_2$, and an aliquot titrated with 0.1 N sodium hydroxide to determine the citric acid concentration. The amount of citric acid in the combined effluent and rinses was determined from this figure, and subtracted from the total amount of citric acid introduced into the column. The resulting figure represented the amount of citric acid adsorbed by the resin.

For the desorption step, 1.5 bed volumes of water were added to the column, and the resin bed agitated with compressed air. Boiling water (100° C.) was circulated through the jacket of the column for about 20 minutes until the internal temperature was at least 85° C. The column was drained and again blown dry with compressed air. After cooling to room temperature, the citric acid recovered from the resin was determined by titration. From this figure and the dry weight of the polymer on the column, the amount of citric acid desorbed per gram of resin was determined.

The results of this testing are shown in Table 1. As demonstrated, the hot water desorption process is highly effective using the polyvinylpyridine weak base polymers. For instance, both REILLEX™ 425 polymer ("R425") and REILLEX™ HP ("RHP") polymer samples exhibited good citric acid desorption capacity, with the former showing greater capacity in this work.

TABLE 1

| Resin | Run | % Acid (Infl.) | Acid Desorbed | Desorption Capacity |
| --- | --- | --- | --- | --- |
| RHP[a] | 1 | 10.2 | 4.17 g | 240 mg/g resin |
|  | 2 | 10.6 | 3.60 g | 207 mg/g resin |
|  | 3 | 10.1 | 4.06 g | 234 mg/g resin |
| R425[b] | 1 | 9.7 | 6.28 g | 302 mg/g resin |
|  | 2 | 9.7 | 5.97 g | 287 mg/g resin |
|  | 3 | 9.7 | 6.36 g | 306 mg/g resin |
| R425[c] | 1 | 10.4 | 3.31 g | 338 mg/g resin |
|  | 2 | 10.4 | 3.27 g | 334 mg/g resin |
|  | 3 | 10.4 | 3.23 g | 330 mg/g resin |

[a]Polymer dry wt. = 17.4 g. Water-wet polymer volume = 62 cc.
[b]Polymer dry wt. = 20.8 g. Water-wet polymer volume = 65 cc.
[c]Polymer dry wt. = 9.8 g. Water-wet polymer volume = 34 cc.

EXAMPLE 2

Desorption Testing for Various Resins

The procedure of Example 1 was repeated, except using the various gel and macroreticular ("macro") resins listed below. In each case the resins demonstrated the ability to effectively adsorb citric acid, and desorption capacities above 100 mg citric acid/g polymer were observed in all cases, and in most cases above 200 mg citric acid/g polymer. Poly(4-vinylpyridine) crosslinked with 8% divinylbenzene (resin No. 2) demonstrated the greatest desorption capacity at well over 300 mg citric acid/g resin. The partially quaternized and N-oxide form resins (Nos. 1 and 6, respectively) demonstrated improved reversibility over their non-modified counterparts (reversibility=desorbed grams citric acid/total grams citric acid adsorbed×100) while still maintaining respectable desorption capacities.

TABLE 2

| No. | Vinylpyridine | Crosslinker/% | Type | Modification |
|---|---|---|---|---|
| 1 | poly-4-vinylpyridine | DVB/25%[a] | macro | 22% quat.[b] |
| 2 | Poly-4-vinylpyridine | DVB/8% | gel | |
| 3 | Poly-2-vinylpyridine | DVB/12% | macro | |
| 4 | Poly-2-methyl-6-vinylpyridine | DVB/8% | gel | |
| 5 | Poly-2-methyl-6-vinylpyridine | DVB/25% | gel | |
| 6 | Poly-4-vinylpyridine | DVB/25% | macro | 25% N-oxide[c] |
| 7 | Poly-2-vinylpyridine | DVB/14% | gel | |
| 8 | Hydrophilic Poly-4-vinylpyridine | DGD/14%[d] | macro | |

[a]DVB = divinylbenzene
[b]22 equivalent % methyl iodide
[c]25 equivalent % N-oxide
[d]DGD = diethylene glycol dimethacrylate

EXAMPLE 3

Desorptions Achieving High Citric Acid Concentration

In this experimentation, it was demonstrated that the desorbate could effectively be used in subsequent desorption steps to obtain mediums having advantageously high concentrations of citric acid. In these experiments, REILLEX™425 polymer was used in processes as described in Example 1, and the collected desorbed fluids were put back in the column after another saturation and rinse cycle, instead of water. Hot water was then again cycled through the jacket as in Example 1 until the internal column temperature reached at least 85° C. Using this technique, a concentration up to about 10% citric acid is achieved in two cycles. Additional cycles can be performed to further increase citric acid concentration, but in applicants work thus far, due to decreasing usable capacity of the resin with each cycle, the best efficiency has been achieved after two cycles.

EXAMPLE 4

Rate of Hot Water Desorption

Another set of experiments was conducted to determine the rate at which citric acid is desorbed from the resin using hot water. Accordingly, processes analogous to those described in Example 1 were performed up to the rinse step. After the rinse step, the resin was removed from the column and transferred to a stirred beaker containing 1.5 bed volumes of boiling water. 3 mL samples of the desorbate were taken at time intervals of 3, 5, 7, 10, 16, 22, and 30 minutes. The samples were weighed and titrated with 0.1N NaOH. The amount of citric acid in the total solution was calculated from the titration results. The fraction of citric acid desorbed at each interval was calculated, regarding the total amount of citric acid in solution at the final sample time as 100%. The results, presented in Table 3 below, demonstrate that the majority of the citric acid desorbed in the total 30 minute treatment was desorbed in the first 5 minutes.

TABLE 3

| Sample Time | % Desorbed |
|---|---|
| 3 minutes | 62 |
| 5 minutes | 80 |
| 7 minutes | 85 |
| 10 minutes | 89 |
| 16 minutes | 91 |
| 22 minutes | 95 |
| 30 minutes | 100 |

EXAMPLE 5

Effect of Salts on Desorption Capacity

Three experiments were done to determine the effect of nutrients (salts) on resin performance. REILLEX™425 polymer was used, and the procedure was the same as outlined above in Example 1 except salt was added to the citric acid solution before saturating the column. A first experiment was performed using 6000 ppm NaCl. Two additional experiments were performed using citric acid solutions with the following nutrient mixture:

38 ppm potassium chloride
50 ppm calcium(II) as chloride salt
70 ppm potassium phosphate, monobasic
0.10 ppm copper(II) as sulfate
0.10 ppm zinc(II) as sulfate
0.10 ppm iron(III) as ammonium citrate
500 ppm magnesium sulfate.

In each case, it was discovered that the resins retained at least about 70% of their desorption capacity under the conditions of this experimentation. Further, the effect of salt concentration did not appear to be significant from applicants' work.

Still another analysis was performed to determine how much ash, from the nutrients, is washed off the resin in the rinse step and thus excluded from the product stream. For these experiments, the ash in the influent in the above three salt experiments was compared to the ash in the desorbate. Each of the mixtures was reduced in ash content approximately 80–90%. This is highly advantageous as it decreases the load on a deashing unit and therefore decreases associated operating costs. Further, this can result in about a 10-fold longer use of the deashing unit before regeneration is necessary.

In another set of experiments, the procedure of Example 1 was again repeated except using corn sugar and molasses broth in respective runs instead of the 10% citric acid solution. Good desorption capacities were again demonstrated, with results being similar to those obtained with the salt-containing citric acid solution described above in this Example. Also, the readily carbonizable impurities ("RCS") contents of the desorbed products were consistently dramatically reduced, e.g. about 65% or more in molasses broth experiments and about 85–90% in the corn sugar broth experiments.

EXAMPLE 6

Regeneration of Polymer

In this set of experiments, the ability to efficiently regenerate the resin after use in adsorption and desorption steps (as described in Example 1) was demonstrated. REILLEX™425 polymer was the polymer first employed in these experiments. Accordingly, 1 liter of 10% $H_2SO_4$ was passed through a column containing a used sample of this resin at 6 bed volumes per hour with intermittent agitation. The resin was then rinsed with water. 1 liter of 4% NaOH was then added, at a rate of 1 bed volume per hour with intermittent agitation. The resin was again rinsed with water, and the NaOH treatment repeated. The resin was left to soak in the 4% NaOH for 36 hrs, where after the resin was rinsed with excess water. In subsequent testing, the resin was shown to have recovered 99% of its initial capacity.

In another experiment, it was shown that the REILLEX™425 polymer used in previous adsorption and desorption steps (as in Example 1) could be regenerated to 100% of its initial capacity using an alternative simple procedure. Accordingly, the used REILLEX™425 polymer was treated in a column with 1 liter of 4% NaOH at 1 bed volume per hour, with intermittent agitation. Thereafter, the resin was rinsed with water until the effluent water was neutral. By this simple procedure, 100% of the initial capacity of the HP resin was regained.

EXAMPLE 7

Regeneration of Polymer

Reillex™425 polymer used in previous adsorption and desorption steps (e.g. Ex. 1) was backwashed with water for 5 minutes at 50% bed expansion. 145 Grams of a 4% NaOH solution per liter of resin was then passed through the column at a flow rate of 2–4 bed volumes per hour. The resin was then rinsed slowly by passing 1.5 bed volumes of water through the column at 2–4 bed volumes/hr. Subsequently, 4 bed volumes of water were passed through the resin at a rate of 16 bed volumes/hour. The resulting resin was found to have 100% of its initial capacity for citric acid.

EXAMPLE 8

Steam Desorption of Citric Acid

A steam desorption apparatus was constructed including a 1½ inch outer diameter stainless steel pipe about 20 inches long. The upper end of the pipe was fitted with a valved steam inlet port and a pressure gauge. The lower end was fitted with a pressure regulation valve. A 14-inch stainless steel water cooled condenser was also attached below the pressure regulation valve. A fine stainless steel wire mesh was positioned in the lower end of the pipe to hold the polymer within the pipe. The apparatus was attached to a pressure regulated high pressure steam line.

One liter of a 10% aqueous solution of citric acid was prepared. 50.0 grams (dry basis) REILLEX™425 polymer were added to the solution and the solution stirred for about 3 hours at ambient temperature. The polymer was filtered off and washed with 250 ml of 5° C. carbonated water. The filtrate was analyzed by titration, whereby it was determined that 60.5 grams of citric acid had been loaded onto the polymer (e.g. acid loading=grams acid in original solution less grams acid in filtrate). The loaded polymer was then placed into the steam desorption apparatus (filling about ⅔ the volume of the pipe), and the outer surface of the apparatus was then heated with live steam. After this, steam was passed through the apparatus at 10–15 psig and a flow rate of about 2 bed volumes per hour (as measured by rate of liquid collection). 100 ml fractions were collected, and each was titrated with 0.1N NaOH. Upon analysis, it was determined that 19.7 g of citric acid were recovered within the first 3 bed volumes of steam collected. This represents a 33% recovery of citric acid from the polymer in the first 3 bed volumes, and gave a citric acid fraction of greater than 5% by weight citric acid. The high efficacy of the steam desorption procedure was thus demonstrated.

EXAMPLE 9

Stronger Acid Desorption of Citric Acid

A column containing REILLEX™425 resin was prepared as in Example 1. A 10% citric acid solution was passed through the column until saturation, and the saturated resin rinsed with $CO_2$ water, also as in Example 1. A 10% solution of sulfuric acid was prepared and passed through the resin bed in the column while the pH of the column effluent was monitored. After the pH dropped to 1, flow was discontinued (at this point, a 150ml citric acid fraction had been collected). HPLC analysis of the citric acid fraction indicated that it contained 11.3g of citric acid, and 1.6 g sulfuric acid. Thus >99% of the adsorbed citric acid was removed from the polymer prior to any significant presence of the stronger acid in the effluent, and a 7.4 weight % citric acid desorbed product medium was obtained. Further, in similar experiments employing molasses and corn sugar broth instead of the prepared 10% citric acid solution, analysis of the products showed that both ash and RCS content were very substantially reduced. For example, ash content was consistently reduced by about 85–90% or more, and RCS content was consistently reduced by about 85%–95% or more. Similar results are obtained when AMBERLIST A-21® resin, commercially available from Rohm and Haas Co., Philadelphia, Pa., is used instead of REILLEX®425 resin. This inventive process thus provides highly efficient desorption of citric acid from the resin, and a citric acid-rich product medium substantially and unexpectedly free from contamination by the stronger acid or other impurities.

EXAMPLE 10

Resin Stability and Reversibility Testing

Resin stability under processing conditions and the reversibility of the resin (reversibility=desorbed grams citric acid/total grams citric acid adsorbed×100) are vital to the commercial viability of a hot $H_2O$-based citric acid recovery process. In this set of experiments, these two properties of resins embodied by the hot water desorption processes of the present invention were compared to the same properties of other resins.

10% aqueous citric acid solutions were prepared and their concentrations accurately determined by titrating with 0.2 N NaOH to a phenolphthalein endpoint. Each resin to be tested was accurately weighed out 30 to 50 cc and slurried with water in a jacketed 1" diameter ion-exchange column with volume markings. The post-slurry procedures of Example 1 were then repeated using three resin samples. For comparative purposes, ADSORBATE VP-8 and ADSORBATE VI-9 polymers (Riedel-de-Haen), which are not within the preferred inventive hot $H_2O$ desorption process, were used in testing alongside the REILLEX 425 polymer. The ADSORBATE VP-8 polymer includes poly(4-vinylpyridine) copolymerized with acetamide derivative, interlaced with trimethylolpropane triacrylate, and is 8% crosslinked. The ADSORBATE VI-9 polymer is a poly(vinylimidazole) copolymerisate with an acetamide derivative interlaced with N,N'-methylenediacrylamide, and is 9% crosslinked.

The results of this testing are set forth in Tables 4 through 8 below. Tables 4 and 5 show the citric acid desorption capacities of the VP-8 resin and the VI-9 resin, respectively, over 6 adsorption/desorption runs. In Tables 4 and 5, "BV"=bed volume and "CA"=citric acid. Table 6 shows a comparison of the reversibility of the VP-8 resin and the VI-9 resin to that of the REILLEX 425 resin. As can be seen, the reversibilities of the VP-8 and VI-9 resins are highly inferior, measuring at 15.5% and 16.2% respectively as compared to the 33% figure for the REILLEX 425 resin. Additionally, the desorbate acid concentrations for the VP-8 and VI-9 resins are inferior. These factors severely impact process economics using the VP-8 and VI-9 polymers, making them highly disadvantageous as compared to polymers of the present invention. Tables 7 and 8 show particle size distributions for the VP-8 resin before and after the 6 runs, respectively, and demonstrate a further disadvantage—it is unstable to physical degradation under hot $H_2O$ desorption conditions of the invention. The particles of the VP-8 resin suffered substantial breakdown as shown by the mean particle size before (61.50 um) and after (56.89 um) the 6 adsorption/desorption cycles and the occurrence of higher percentages of polymer in lower particle size ranges after the process cycles.

These comparative studies demonstrate the superiority of the applicants' processes involving hot $H_2O$ desorption and the use of stable, divinylbenzene-crosslinked resins. The applicants' claimed resins suffer no substantial particle breakdown enabling their extended use and also provide superior desorbate acid concentration and reversibility.

EXAMPLE 11

This example demonstrates the ability to perform preferred stronger acid desorptions at high temperatures. Example 9 was repeated, except a 0.3% sulfuric acid medium was used as the desorbing agent at a temperature of about 90° C. Again, nearly all citric acid on the column could be removed prior to the appearance of any sulfuric acid in the desorbed fractions.

TABLE 4

Citric Acid Desorption Capacity of Vp-8[a]

| Run | BV CC | Swelling % | Desorbed CA, g | Desorption mg CA/g resin | Capacity mg CA/cc resin |
|---|---|---|---|---|---|
| 1 | 74 | 125 | 3.72 | 203 | 116 |
| 2 | 72 | 125 | 4.32 | 237 | 136 |
| 3 | 78 | 144 | 4.24 | 232 | 132 |
| 4 | 80 | 150 | 3.94 | 216 | 123 |
| 5 | 80 | 150 | 4.31 | 235 | 134 |
| 6 | 62 | 92 | 4.27 | 233 | 133 |
| Avg. |  | 130 |  | 266 | 128 |

[a], Wet free base volume, 32 cc = 18.3 g dry weight

TABLE 5

Citric Acid Desorption Capacity of Vp-9[a]

| Run | BV CC | Swelling % | Desorbed CA, g | Desorption mg CA/g resin | Capacity mg CA/cc resin |
|---|---|---|---|---|---|
| 1 | 42 | 10 | 2.03 | 253 | 53.4 |
| 2 | 42 | 10 | 2.52 | 314 | 66.3 |
| 3 | 42 | 10 | 2.36 | 295 | 62.1 |
| 4 | 42 | 10 | 2.51 | 313 | 66.0 |
| 5 | 42 | 10 | 2.79 | 348 | 73.4 |
| 6 | 42 | 10 | 2.34 | 292 | 61.5 |
| Avg. |  | 10 |  | 302 | 63.8 |

[a], Wet free base volume, 38 cc = g dry weight

TABLE 6

Comparison of Resin Properties

| Property | REILLEX ® 425 Polymer | VP-8 | VI-9 |
|---|---|---|---|
| Reversibility | 33% | 15.5% | 16.2% |
| Desorbate Conc. | 6.4% | 3.8% | 3.2% |
| Citric Acid Desorption Capacity | 95 mg/cc | 128 mg/cc | 63.8 mc/cc |

TABLE 7

| Size Range μm | Result In % | Result Below % |
|---|---|---|
| 0.50–1.32 | 0.06 | 0.06 |
| 1.32–1.60 | 0.15 | 0.21 |
| 1.60–1.95 | 0.21 | 0.42 |
| 1.95–2.38 | 0.20 | 0.62 |
| 2.38–2.90 | 0.16 | 0.78 |
| 2.90–3.53 | 0.10 | 0.88 |
| 3.53–4.30 | 0.06 | 0.95 |
| 4.30–5.24 | 0.04 | 0.99 |
| 5.24–6.39 | 0.05 | 1.04 |
| 6.39–7.78 | 0.07 | 1.11 |
| 7.78–9.48 | 0.01 | 1.21 |
| 9.48–11.55 | 0.16 | 1.36 |
| 11.55–14.08 | 0.26 | 1.62 |
| 14.08–17.15 | 0.39 | 2.01 |
| 17.15–20.90 | 0.53 | 2.54 |
| 20.90–25.46 | 0.66 | 3.20 |
| 25.46–31.01 | 0.78 | 3.98 |
| 31.01–37.79 | 1.12 | 5.11 |
| 37.79–46.03 | 2.03 | 7.14 |
| 46.03–56.09 | 3.76 | 10.91 |
| 56.09–68.33 | 6.44 | 17.35 |
| 68.33–83.26 | 10.10 | 27.45 |
| 83.26–101.44 | 14.01 | 41.46 |
| 101.44–123.59 | 16.27 | 57.72 |
| 123.59–150.57 | 15.50 | 73.22 |
| 150.57–183.44 | 12.56 | 85.78 |
| 183.44–223.51 | 8.24 | 94.02 |
| 223.51–272.31 | 4.27 | 98.29 |
| 272.31–331.77 | 1.54 | 99.83 |
| 331.77–404.21 | 0.17 | 100.00 |
| 404.21–492.47 | 0.00 | 100.00 |
| 492.47–600.00 | 0.00 | 100.00 |

TABLE 8

| Size Range μm | Result In % | Result Below % |
|---|---|---|
| 0.50–1.32 | 0.07 | 0.07 |
| 1.32–1.60 | 0.17 | 0.24 |
| 1.60–1.95 | 0.22 | 0.47 |
| 1.95–2.38 | 0.21 | 0.68 |

TABLE 8-continued

| Size Range μm | Result In % | Result Below % |
|---|---|---|
| 2.38–2.90 | 0.16 | 0.84 |
| 2.90–3.53 | 0.11 | 0.95 |
| 3.53–4.30 | 0.07 | 1.02 |
| 4.30–5.24 | 0.04 | 1.06 |
| 5.24–6.39 | 0.03 | 1.10 |
| 6.39–7.78 | 0.04 | 1.13 |
| 7.78–9.48 | 0.08 | 1.21 |
| 9.48–11.55 | 0.19 | 1.40 |
| 11.55–14.08 | 0.33 | 1.73 |
| 14.08–17.15 | 0.51 | 2.24 |
| 17.15–20.90 | 0.77 | 3.01 |
| 20.90–25.46 | 1.07 | 4.08 |
| 25.46–31.01 | 1.23 | 5.31 |
| 31.01–37.79 | 1.31 | 6.62 |
| 37.79–46.03 | 1.99 | 8.61 |
| 46.03–56.09 | 3.57 | 12.18 |
| 56.09–68.33 | 6.03 | 18.21 |
| 68.33–83.26 | 10.23 | 28.44 |
| 83.26–101.44 | 16.64 | 45.07 |
| 101.44–123.59 | 21.09 | 66.16 |
| 123.59–150.57 | 17.60 | 83.76 |
| 150.57–183.44 | 10.63 | 94.40 |
| 183.44–223.51 | 4.52 | 98.82 |
| 223.51–272.31 | 1.08 | 100.00 |
| 272.31–331.77 | 0.00 | 100.00 |
| 331.77–404.21 | 0.00 | 100.00 |
| 404.21–492.47 | 0.00 | 100.00 |
| 492.47–600.00 | 0.00 | 100.00 |

What is claimed is:

1. A process for treating a medium to recover citric acid therein contained, comprising contacting the medium with a solid-phase free base polymer having tertiary amine functions to adsorb the citric acid, after said contacting, rinsing said free base polymer having tertiary amine functions with an aqueous rinse medium, and after said rinsing, desorbing the citric acid by displacement by passing an aqueous solution of a stronger acid over the polymer so as to form an effluent containing citric acid, collecting the effluent into a citric acid-containing fraction, and ceasing collection of the effluent into the citric acid-containing fraction prior to there being any significant presence of the stronger acid in the effluent, so that the citric acid-containing fraction remains substantially free from contamination by the stronger acid.

2. A process according to claim 1, wherein said free base polymer having tertiary amine functions is a poly 2- or poly 4-vinylpyridine polymer.

3. A process according to claim 2, wherein said poly 2- or poly 4-vinylpyridine polymer is a crosslinked bead-form gel or macroreticular resin.

4. A process according to claim 3, wherein said poly 2- or poly 4-vinylpyridine polymer is at least about 2% crosslinked with divinylbenzene.

5. A process according to claim 4, wherein said free base polymer having tertiary amine functions is a poly 2-vinylpyridine polymer.

6. A process according to claim 4, wherein said free base polymer having tertiary amine functions is a poly 4-vinylpyridine polymer.

7. A process according to claim 4, wherein said adsorbing is at a temperature below about 25° C.

8. A process according to claim 7, and also including the step of rinsing said free base polymer having tertiary amine functions with an aqueous rinse medium between said adsorption and desorption steps.

9. A process according to claim 8, wherein said rinsing is at a temperature below about 15° C. and said aqueous rinse medium exhibits a pH below about 4.5.

10. A process according to claim 9, wherein said aqueous rinse medium contains $CO_2$.

11. A process according to claim 1, which comprises:

passing the citric acid-containing medium through a contact zone filled with a particulate solid-phase divinylbenzene-crosslinked polymer having attached pyridine functions or attached aliphatic tertiary amine functions, said citric acid-containing medium being at a temperature below about 40° C. during said passing so as to adsorb citric acid on the polymer, said passing being continued until the polymer in the contacting zone is substantially fully loaded with citric acid; and, after said passing, rinsing said polymer with an aqueous rinse medium; and, after said rinsing, displacing the adsorbed citric acid with aqueous sulfuric acid so as to provide a desorbed aqueous medium containing at least 5% by weight citric acid and being substantially free from sulfuric acid.

12. The process of claim 11 wherein said aqueous sulfuric acid is at a temperature above about 75 C during said displacing.

13. A process for effectively recovering citric acid in a readily purifiable form from a medium in which it is contained, with good desorption capacity and regenerability of a polymer adsorbent, comprising:

passing the citric acid-containing medium through a contact zone filled with a particulate solid-phase divinylbenzene-crosslinked polymer having attached pyridine functions or attached aliphatic tertiary amine functions, said citric-acid containing medium being at a temperature below about 40° C. during said passing so as to adsorb citric acid on the polymer, said passing being continued until the polymer in the contacting zone is substantially fully loaded with citric acid; and, desorbing the adsorbed citric acid with hot $H_2O$ at a temperature above about 75° C. so as to provide a desorbed product consisting essentially of an aqueous solution of citric acid containing at least about 5% by weight citric acid, and wherein the particulate divinylbenzene-crosslinked polymer having attached pyridine functions or attached aliphatic tertiary amine functions is stable against physical degradation under the conditions of said desorbing.

14. A process according to claim 13, wherein said free base polymer having tertiary amine functions is a poly 2- or poly 4-vinylpyridine polymer.

15. A process according to claim 13, wherein said desorbing is at a temperature of at least about 85° C.

16. A process according to claim 15, wherein said poly 2- or poly 4-vinylpyridine polymer is a crosslinked polymer.

17. A process according to claim 16, wherein said poly 2- or poly 4-vinylpyridine is a bead-form gel or macroreticular resin.

18. A process according to claim 16, wherein said poly 2- or poly 4-vinylpyridine polymer is crosslinked with divinylbenzene.

19. A process according to claim 18, wherein said poly 2- or poly 4-vinylpyridine polymer is at least about 8% crosslinked with divinylbenzene.

20. A process according to claim 19, wherein said free base polymer having tertiary amine functions is a poly 2-vinylpyridine polymer.

21. A process according to claim 19, wherein said free base polymer having tertiary amine functions is a poly 4-vinylpyridine polymer.

22. A process according to claim 19, wherein said poly 2- or poly 4-vinylpyridine polymer is a gel resin.

23. A process according to claim 19, wherein said poly 2- or poly 4-vinylpyridine polymer is a macroreticular resin.

24. A process according to claim 19, wherein said poly 2- or poly 4-vinylpyridine polymer has a desorption capacity of at least about 200 milligrams citric acid per gram polymer.

25. A process according to claim 19, wherein at least about 25% of the citric acid adsorbed on the polymer is desorbed during said desorbing step.

26. A process according to claim 24, wherein at least about 25% of the citric acid adsorbed on the polymer is desorbed during said desorbing step.

27. A process according to claim 25, wherein said adsorbing is at a temperature below about 25° C.

28. A process according to claim 27, wherein said desorbing step provides an aqueous medium containing at least about 2% by weight citric acid.

29. A process according to claim 28, wherein said free base polymer having tertiary amine functions also contains pendant pyridine N-oxide groups.

30. A process according to claim 28, wherein said polyvinylpyridine polymer also contains pendant quaternized pyridine groups.

31. A process according to claim 28, and also including the step of rinsing said free base polymer having tertiary amine functions with an aqueous rinse medium between said adsorption and desorption steps.

32. A process according to claim 31, wherein said rinsing is at a temperature below about 15° C. and said aqueous rinse medium exhibits a pH below about 4.5.

33. A process according to claim 32, wherein said aqueous rinse medium contains $CO_2$.

34. A process according to claim 28, wherein said desorption step is conducted using the desorbate medium of a previous desorption step to increase the amount of citric acid in said desorbate medium.

35. A process according to claim 28, wherein said free base polyvinylpyridine polymer is a poly 4-vinylpyridine crosslinked with about 25% divinylbenzene exhibiting a macroreticular bead form.

36. A process according to claim 28, wherein said free base polyvinylpyridine polymer is a poly 4-vinylpyridine crosslinked with about 8% divinylbenzene exhibiting a gel bead form.

37. A process for effectively recovering citric acid in a readily purifiable form from a medium in which it is contained, with good desorption capacity and regenerability of a polymer adsorbent, comprising:

passing the citric acid-containing medium through a contact zone filled with a particulate solid-phase of a 2% or more divinylbenzene crosslinked poly-2- or poly-4-vinylpyridine polymer, said citric-acid containing medium being at a temperature below about 40° C. during said passing so as to adsorb citric acid on the polymer; and, passing hot $H_2O$ through the contacting zone at a temperature above about 75° C. so as to provide a desorbed fraction consisting essentially of an aqueous solution of citric acid containing at least about 5% by weight citric acid, and wherein the particulate divinylbenzene-crosslinked polymer having attached pyridine functions is stable against physical degradation under the conditions of said desorbing.

38. A process for recovering citric acid from a medium in which it is contained, comprising:

providing a contact zone filled with a particulate solid-phase polymer having attached pyridine functions or attached aliphatic tertiary amine functions, said particulate solid-phase polymer being at least 2% crosslinked with divinylbenzene;

a low-temperature passing step including passing the citric acid-containing medium through the contacting zone at a temperature below about 40° C.; and, a high-temperature passing step including passing water or an aqueous feed containing citric acid through the contacting zone at a temperature above about 75° C., so as to provide an aqueous medium containing citric acid; and wherein said polymer is stable against physical degradation under the conditions of said low-temperature and high-temperature passing steps.

39. The process of claim 38 wherein the polymer has pendant pyridine functions.

40. The process of claim 39 wherein the polymer is a vinylpyridine polymer.

* * * * *